US007017622B2

(12) United States Patent
Osborne et al.

(10) Patent No.: US 7,017,622 B2
(45) Date of Patent: Mar. 28, 2006

(54) AUTOMATED MEANS FOR REMOVING, PARKING AND REPLACING A SYRINGE TIP CAP FROM A SYRINGE

(75) Inventors: Joel A. Osborne, Oklahoma City, OK (US); William C. Aven, Edmond, OK (US); Dennis Tribble, Oklahoma City, OK (US)

(73) Assignee: ForHealth Technologies, Inc., Daytona Beach, FL (US)

( * ) Notice: Subject to any disclaimer, the term of this patent is extended or adjusted under 35 U.S.C. 154(b) by 336 days.

(21) Appl. No.: 10/426,910

(22) Filed: Apr. 30, 2003

(65) Prior Publication Data

US 2004/0104243 A1    Jun. 3, 2004

Related U.S. Application Data

(60) Provisional application No. 60/430,481, filed on Dec. 3, 2002.

(51) Int. Cl.
B65B 1/04      (2006.01)

(52) U.S. Cl. .......................... 141/27; 141/94; 604/407; 604/416

(58) Field of Classification Search ............. 141/2, 141/18, 21–27, 94, 100, 104; 604/407, 411, 604/416
See application file for complete search history.

(56) References Cited

U.S. PATENT DOCUMENTS

| 2,880,723 | A | 4/1959 | Adams |
| 2,981,432 | A | 4/1961 | Flood |
| 3,200,486 | A | 8/1965 | Shields |
| 3,527,017 | A | 9/1970 | Taylor et al. |
| 3,736,933 | A | 6/1973 | Szabo |
| 3,823,818 | A | 7/1974 | Shaw |
| 3,835,897 | A | 9/1974 | Gess |
| 3,848,485 | A | 11/1974 | Grenci |
| 3,865,236 | A | 2/1975 | Rycroft |
| 3,880,211 | A | 4/1975 | Gess |
| 4,472,357 | A | 9/1984 | Levy et al. |
| 4,502,616 | A | 3/1985 | Meierhoefer |
| 4,512,475 | A | 4/1985 | Federighi |
| 4,624,148 | A | 11/1986 | Averette |
| 4,639,250 | A | 1/1987 | Rycroft |
| 4,674,652 | A | 6/1987 | Aten et al. |
| 4,758,230 | A | 7/1988 | Rycroft |
| 4,773,285 | A | 9/1988 | Dionne |
| 4,861,335 | A | 8/1989 | Reynolds |
| 4,865,592 | A | 9/1989 | Rycroft |
| 4,944,736 | A | 7/1990 | Holtz |
| 5,040,437 | A | 8/1991 | Mueller |
| 5,256,154 | A | 10/1993 | Liebert et al. |
| 5,341,854 | A | 8/1994 | Zezulka et al. |
| 5,356,393 | A | 10/1994 | Haber et al. |
| 5,496,288 | A | 3/1996 | Sweeney |
| 5,542,935 | A | 8/1996 | Unger et al. |
| 5,597,530 | A | 1/1997 | Smith et al. |

(Continued)

*Primary Examiner*—Steven O. Douglas
(74) *Attorney, Agent, or Firm*—Darby & Darby

(57) ABSTRACT

In one exemplary embodiment, an automated syringe preparation mechanism for an automated medication preparation system is provided and the mechanism includes (1) a first automated gripping mechanism having a pair of adjustable gripper arms for removing a tip cap from a barrel of one syringe and placing the removed tip cap at a first location and (2) a second automated gripping mechanism having a pair of adjustable gripper arms for replacing the removed tip cap on the syringe barrel after the medication is injected therein.

20 Claims, 5 Drawing Sheets

U.S. PATENT DOCUMENTS

| | | |
|---|---|---|
| 5,651,775 A | 7/1997 | Walker et al. |
| 5,704,921 A | 1/1998 | Carilli |
| 5,735,181 A | 4/1998 | Anderson |
| 5,805,454 A | 9/1998 | Valerino, Sr. et al. |
| 5,826,409 A | 10/1998 | Slepicka et al. |
| 5,855,839 A | 1/1999 | Brunel |
| 5,899,889 A | 5/1999 | Futagawa et al. |
| 5,911,252 A | 6/1999 | Cassel |
| 6,027,472 A | 2/2000 | Kriesel et al. |
| 6,048,086 A | 4/2000 | Valerino, Sr. |
| 6,068,614 A | 5/2000 | Kimber et al. |
| 6,142,039 A | 11/2000 | Herring, Sr. |
| 6,915,823 B1 * | 7/2005 | Osborne et al. ............ 141/27 |
| 2002/0020459 A1 | 2/2002 | Baldwin et al. |

* cited by examiner

AUTOMATED MEANS FOR REMOVING, PARKING AND REPLACING A SYRINGE TIP CAP FROM A SYRINGE

CROSS-REFERENCE TO RELATED APPLICATION

This application claims the benefit of U.S. patent application Ser. No. 60/430,481, filed Dec. 3, 2002, which is hereby incorporated by reference in its entirety.

TECHNICAL FIELD

The present invention relates generally to medical equipment, and more particularly, to an automated apparatus for removing, parking and replacing a tip cap from a syringe.

BACKGROUND

Disposable syringes are in widespread use for a number of different types of applications. For example, syringes are used not only to withdraw a fluid (e.g., blood) from a patient but also to administer a medication to a patient. In the latter, a cap or the like is removed from the syringe and a unit dose of the medication is carefully measured and then injected or otherwise disposed within the syringe.

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved. This results in reduced production costs and also permits the system to operate over any time period of a given day with only limited operator intervention for manual inspection to ensure proper operation is being achieved. Such a system finds particular utility in settings, such as large hospitals, that require a large number of doses of medications to be prepared daily. Traditionally, these doses have been prepared manually in what is an exacting but tedious responsibility for a highly skilled staff. In order to be valuable, automated systems must maintain the exacting standards set by medical regulatory bodies, while at the same time simplifying the overall process and reducing the time necessary for preparing the medications.

Because syringes are often used as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a vial that is sealed with a safety cap or the like. In conventional medication preparation, a trained person retrieves the correct vial from a storage cabinet or the like, confirms the contents and then removes the safety cap manually. This is typically done by simply popping the safety cap off with ones hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe.

FIG. 1 illustrates an exemplary conventional syringe 10 that includes a barrel 20 having an elongated body 22 that defines a chamber 30 that receives and holds a medication that is disposed at a later time. The barrel 20 has an open proximal end 24 with a flange 25 being formed thereat and it also includes an opposing distal end 26 that has a barrel tip 28 that has a passageway 29, that is an ANSI standard luer fitting, formed therethrough. One end of the passageway 29 opens into the chamber 30 to provide communication between the barrel tip 28 and the chamber 30 and the opposing end of the passageway 29 is open to permit the medication to be dispensed through a cannula (not shown) or the like that is later coupled to the barrel tip 28.

An outer surface of the barrel tip 28 can include features to permit fastening with a cap or other type of enclosing member. For example, the outer surface can have threads 27 that permit a tip cap 40 to be securely and removably coupled to the barrel tip 28. The tip cap 40 thus must have complementary fastening features that permit it to be securely coupled to the barrel tip 28. The tip cap 40 is constructed so that it closes off the passageway 29 to permit the syringe 10 to be stored and/or transported with a predetermined amount of medication disposed within the chamber 30. As previously mentioned, the term "medication" refers to a medicinal preparation for administration to a patient and most often, the medication is contained within the chamber 30 in a liquid state even though the medication initially may have been in a solid state, which was compounded into a liquid state.

The syringe 10 further includes a plunger 50 that is removably and adjustably disposed within the barrel 20. More specifically, the plunger 50 is also an elongated member that has a proximal end 52 that terminates in a flange 54 to permit a user to easily grip and manipulate the plunger 50 within the barrel 20. Preferably, the plunger flange 54 is slightly smaller than the barrel flange 25 so that the user can place several fingers around, against, or near the barrel flange 25 to hold the barrel 20 and then use the thumb of the certain hand to withdrawn or push the plunger 50 forward within the barrel 20. An opposite distal end 56 of the plunger 50 terminates in a stopper 59 or the like that seals against the inner surface of the barrel 20 within the chamber 30. The plunger 50 can draw a fluid (e.g., air or a liquid) into the chamber 30 by withdrawing the plunger 50 from an initial position where the stopper 59 is near or at the barrel tip 28 to a position where the stopper 59 is near the proximal end 24 of the barrel 20. Such steps may be performed either sequentially or simultaneously by the automated methods. Conversely, the plunger 50 can be used to expel or dispense medication by first withdrawing the plunger 50 to a predetermined location, filling the chamber 30 with medication and then applying force against the flange 54 so as to move the plunger 50 forward within the chamber 30, resulting in a decrease in the volume of the chamber 30 and therefore causing the medication to be forced into and out of the barrel tip 28.

Typically, the medication is placed in the syringe when the needle is in place and secured to the barrel tip by drawing the medication through the needle and into the syringe barrel. Such an arrangement makes it very difficult for this type of syringe to be used in an automated system due to the fact that medication is drawn through the small needle into the syringe barrel and therefore this operation is a very time and labor intensive task. What is needed in the art and has heretofore not been available is a system and method for automating the medication preparation process and more specifically, an automated system and method for preparing a syringe including the automated removal, parking, and replacement of a tip cap of the syringe.

SUMMARY

The present invention provides an automated syringe preparation mechanism for an automated medication preparation system. The mechanism includes a first automated gripping device for removing a tip cap from a barrel tip of one syringe and placing the removed tip cap at a first location remote from the syringe and a second automated gripping device for replacing the removed tip cap on the syringe barrel after medication has been injected or otherwise transferred therein. Each of the first and second automated gripping devices is in communication with a programmable controller and each of the first and second gripping devices moves in at least two directions to accomplish the aforementioned operation. In one exemplary embodiment, each of the first and second automated gripping devices has a first control mechanism for controlling opening and closing of gripper arms that grasp and retain the tip cap. A second control mechanism is provided for controlling up and down movement of the gripping device and a third control mechanism is provided for controlling inward and outward movement of the gripping device.

Further aspects and features of the exemplary automated safety cap removal mechanism disclosed herein can be appreciated from the appended Figures and accompanying written description.

DETAILED DESCRIPTION OF PREFERRED EMBODIMENTS

Figure 2:
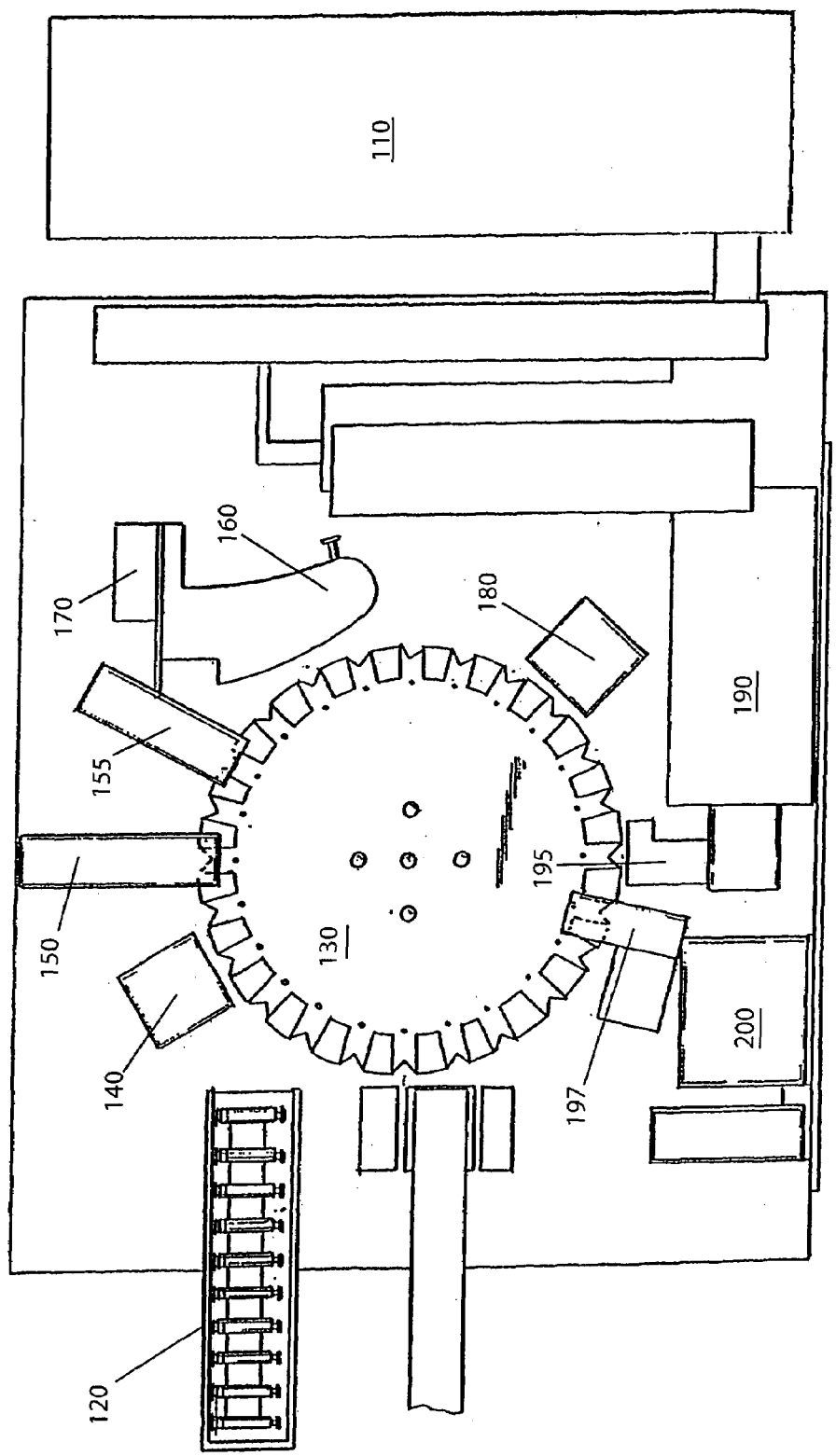
FIG. 2 is a diagrammatic plan view of an automated system for preparing or otherwise compounding a medication to be administered to a patient.

FIG. 2 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing or compounding unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a liquid or fluid diluent is added to form a medicinal composition. Thus, the station 110 functions as a storage unit for storing one or more medications, etc. under proper storage conditions. Typically, medications and the like are stored in sealed containers, such as vials 60 of FIG. 2, that are labeled to clearly indicate the contents of each vial.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, guidance mechanism, etc.

The system 100 also includes a rotary apparatus (dial) 130 for advancing the fed syringes from and to various stations of the system 100. A number of the stations are arranged circumferentially around the rotary apparatus 130 so that the syringe is first loaded at a first station 140 and then rotated a predetermined distance to a next station, etc. as the medication preparation or compounding process advances. At each station, a different operation is performed with the end result being that a unit dose of medication is disposed within the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At the second station 140, the syringes are loaded into one of the nests of the rotary apparatus 130. One syringe is loaded into one nest of the rotary apparatus 130 in which the syringe is securely held in place. The system 100 preferably includes additional mechanisms for preparing the syringe for use, such as removing a tip cap at a third station 150 and extending a plunger of the syringe at another station 155. At this point, the syringe is ready to be filled.

The system 100 also preferably includes a reading device (not shown) that is capable of reading a label disposed on the sealed container containing the medication. The label is read using any number of suitable reader/scanner devices, such as a bar code reader, etc., so as to confirm that the proper medication has been selected from the storage unit of the station 110 (this function is preferably part of the labeled station 195 in FIG. 2). Multiple readers, sensors, or other methods can be employed in the system at various locations to confirm the accuracy of the entire process. Once the system 100 confirms that the sealed container that has been selected contains the proper medication, the container is delivered to a fourth station 160 using an automated mechanism, such a robotic gripping device as will be described in greater detail. At the fourth station 160, the vial is prepared by removing the safety cap from the sealed container and then cleaning the exposed end of the vial. Preferably, the safety cap is removed on a deck of the automated system 100 having a controlled environment. In this manner, the safety cap is removed just-in-time for use.

The system 100 also preferably includes a fifth station 170 for injecting a diluent into the medication contained in the sealed container and then subsequently mixing the medication and the diluent to form the medication composition that is to be disposed into the prepared syringe. At a fluid transfer station, the prepared medication composition is withdrawn from the container (i.e., vial) and is then disposed into the syringe. For example, a cannula can be inserted into the sealed vial and the medication composition then aspirated into a cannula set. The cannula is then withdrawn from the vial and positioned using the rotary apparatus 130 in line with (above, below, etc.) the syringe. The unit dose of the medication composition is then delivered to the syringe, as well as additional diluent if necessary or desired. The tip cap is then placed back on the syringe at a sixth station 180. A seventh station 195 prints and applies a label to the syringe and a device, such as a reader, can be used to verify that this label is placed in a correct location and the printing thereon is readable. Also, the reader can confirm that the label properly identifies the medication composition that is contained in the syringe. The syringe is then unloaded from the rotary apparatus 130 at an unloading station 200 and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 197 located prior to the unloading station 200.

The system 100 preferably includes additional devices for preparing the syringe for use, such as removing a tip cap 40 of the syringe at a third station 150 and then placing or parking the tip cap 40 on the dial (rotary device) 130 of the automated system 100 having a controlled environment. In this manner, the tip cap 40 is removed just-in-time for use. The tip cap 40 is then placed back on the syringe at the sixth station 180.

More specifically, FIGS. 3 through 6 illustrate a device that is used at the third station 150 as well as the sixth station 180. One will understand that the device that is used at the sixth station 180 is preferably the same type of device as the one used at the third station 150 and is merely programmed to operate differently.

Figure 1:
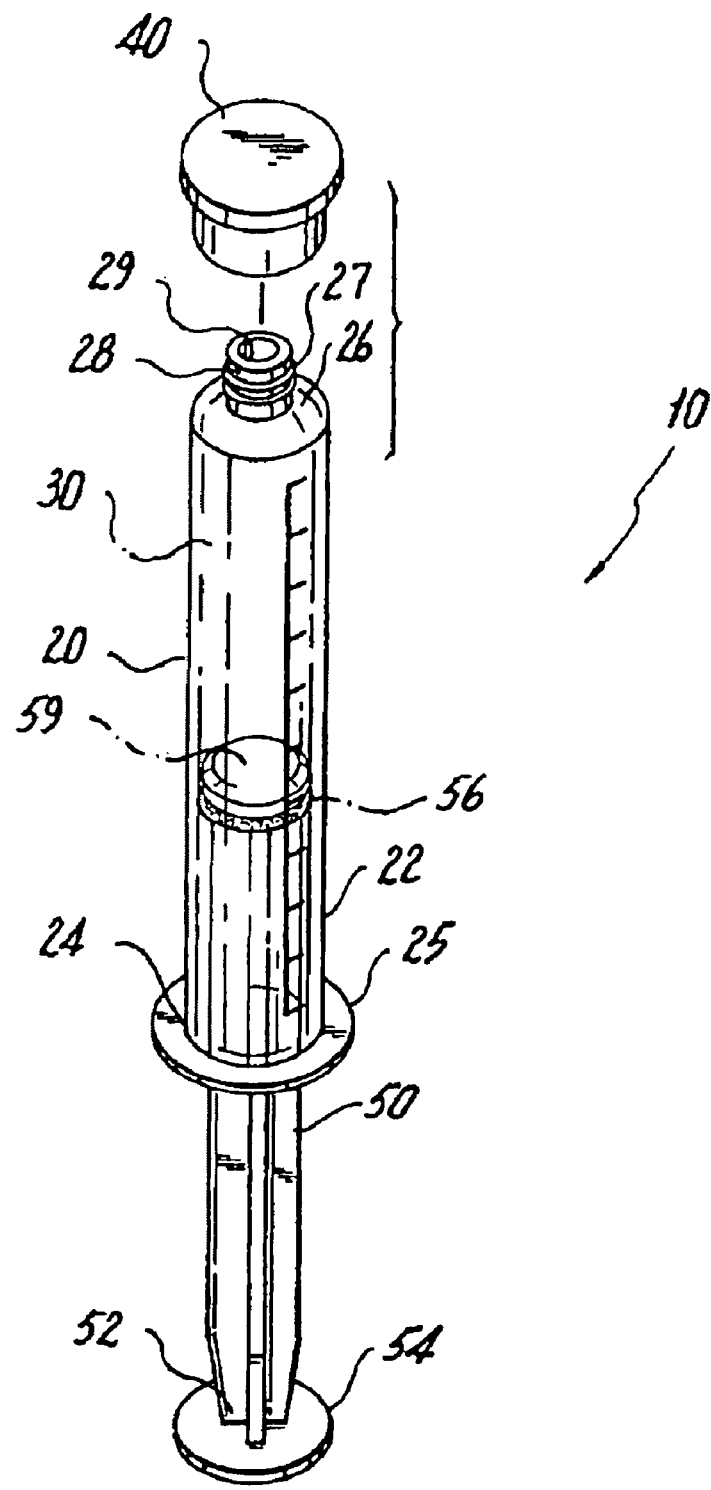
FIG. 1 is a perspective view of a conventional syringe having a safety tip cap removed therefrom.
Figure 3:
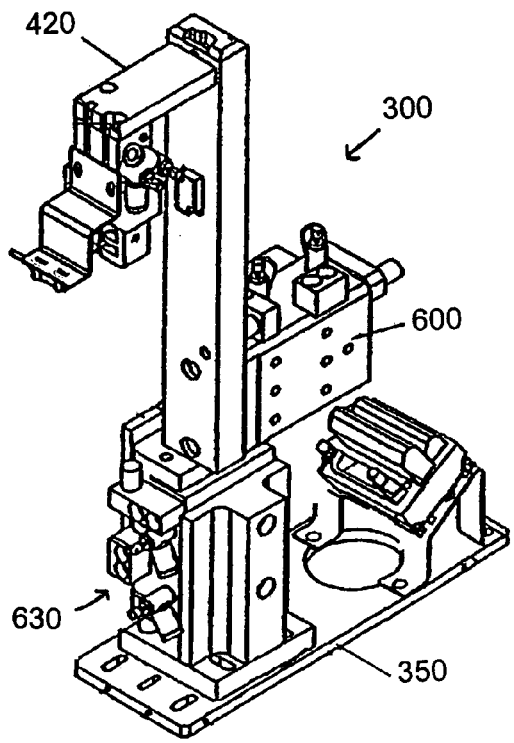
FIG. 3 is a front perspective view of an automated device for removing, parking and replacing a tip cap of a syringe.
Figure 5:
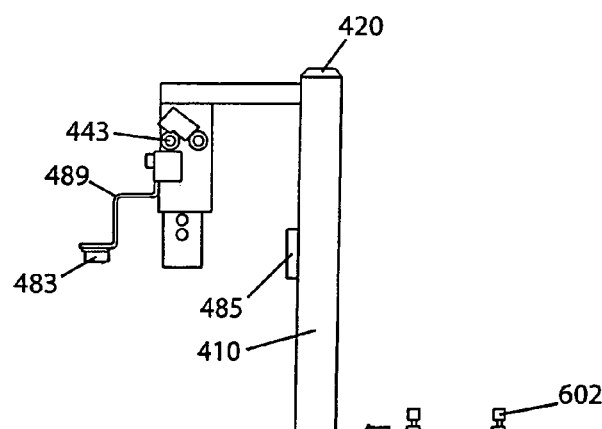
FIG. 5 is a side elevation view of the automated device of FIG. 3.
Figure 5:
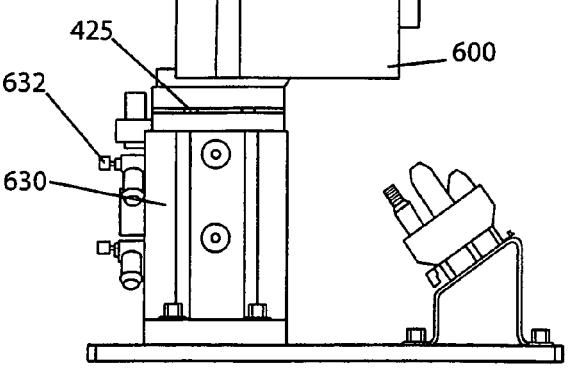
Figure 4:
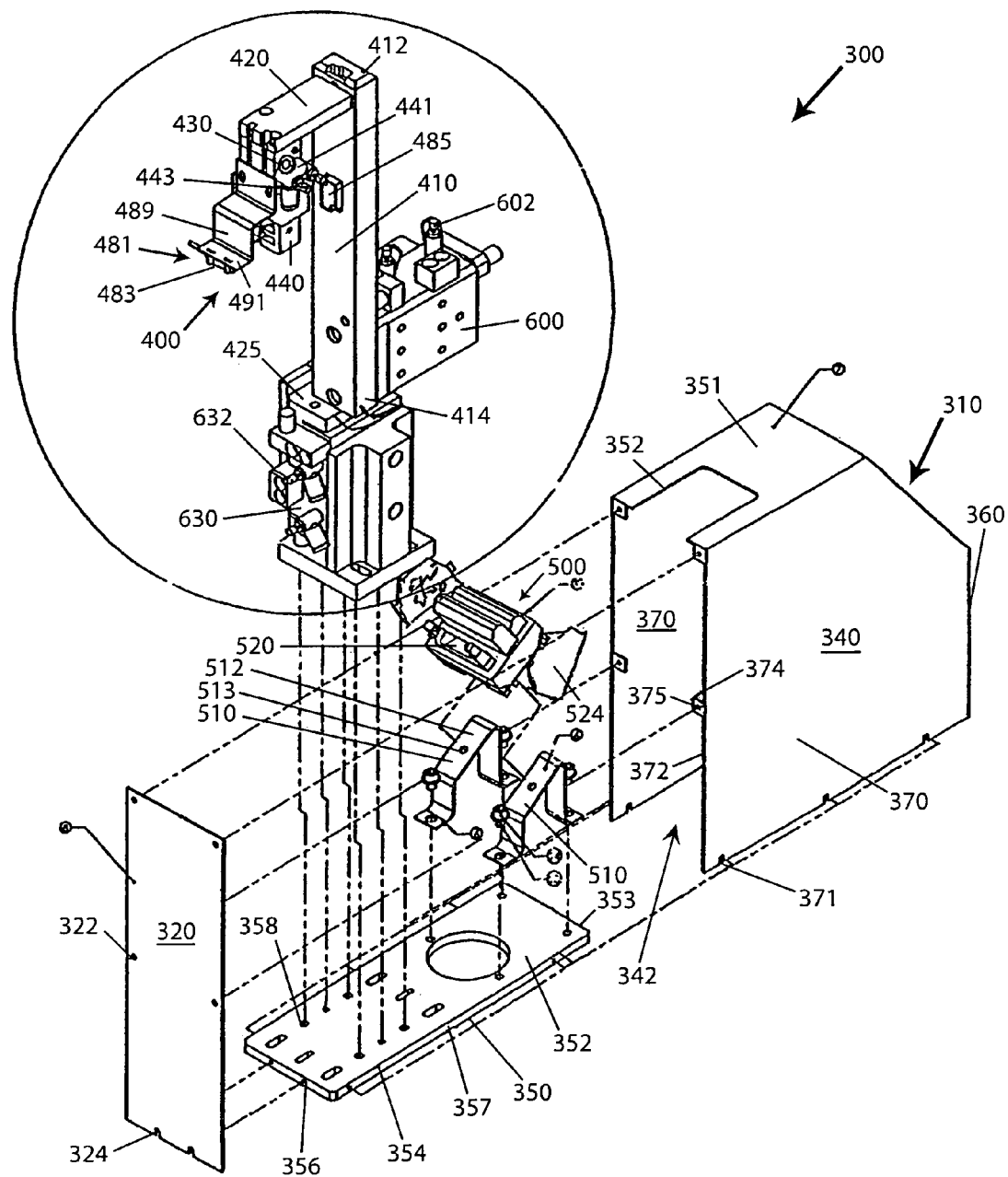
FIG. 4 is an exploded perspective view of the automated device of FIG. 3.
Figure 6:
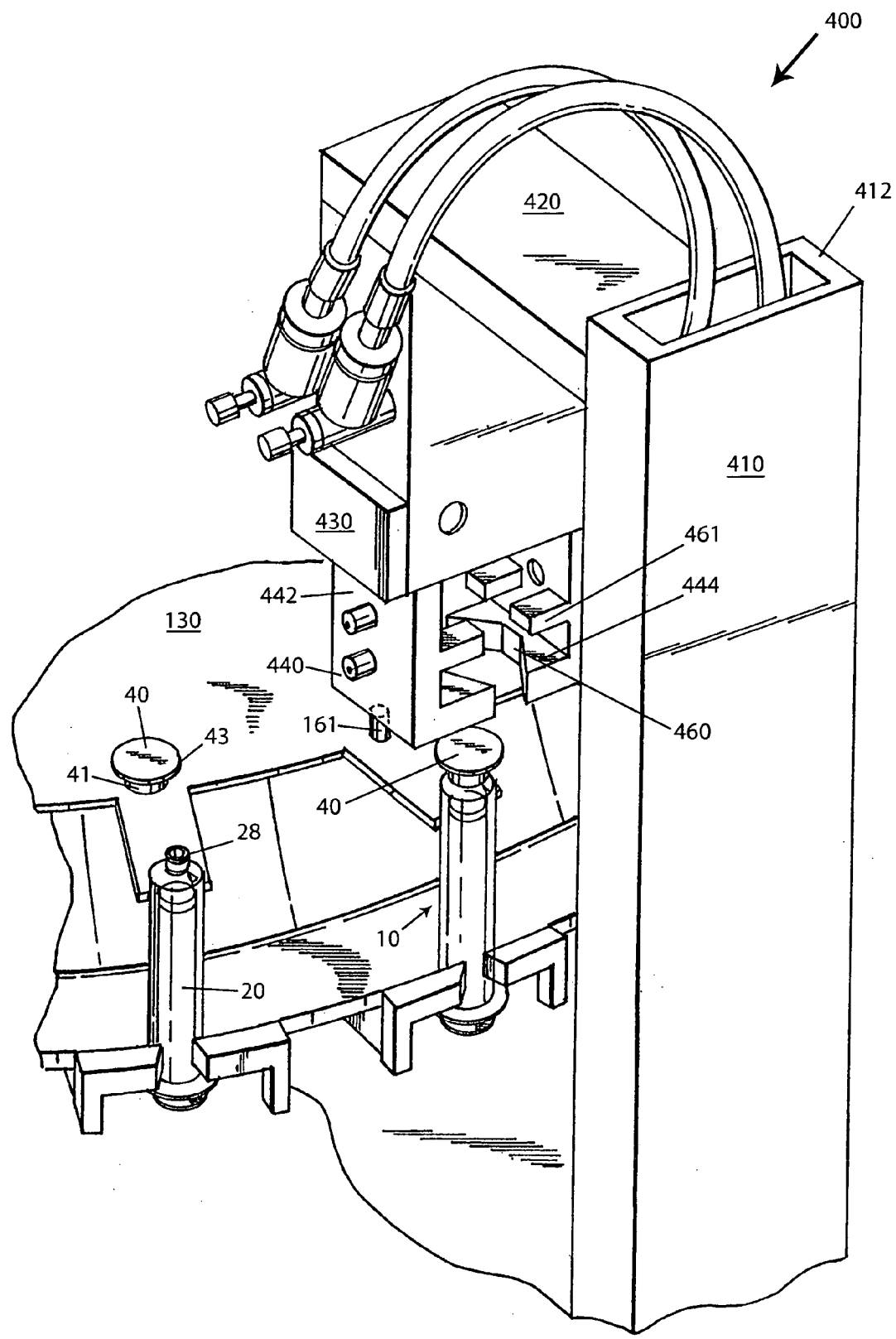
FIG. 6 is a perspective view of a rotary device for carrying syringes from one station to another with an exemplary tip cap replacement station being partially shown.

FIG. 3 is a front perspective view of the device 300 and FIG. 4 is an exploded perspective view of the device 300. The exemplary device 300 is formed of a number of working parts that are operatively connected to one another and are also in communication with a controller 470 that is preferably a programmable unit, such as a personal computer or the like, which controls operation of the device 300 as well as other working components. As best shown in the exploded view of FIG. 4, the device 300 includes a housing 310 and a tip cap gripper unit 400 that engages the tip cap 40 (FIG. 1) and removes it from syringe 10 and then securely places or parks it on the dial 130 before later retrieving the removed tip cap 40 from the dial 130 and then replacing the tip cap 40 on the syringe 10 using a second tip cap gripper unit 400 which is part of another device which is described in detail hereinafter. The gripper unit 400 is partially contained within the housing 310 except for the adjustable gripper parts that lie outside of the housing 310 so that they can engage and remove the tip cap 40 of one syringe 10 as it is advanced along the dial 130 (FIGS. 2 and 6).

The exemplary housing 310 includes a front cover plate 320, a back cover 340 and a base plate 350. The front cover plate 320 is a generally rectangular plate that has a number of openings 322 formed therein to receive fasteners (not shown) which securely couple the front cover plate 320 to the back cover 340. The front cover plate 320 can also include one or more slots 324 that also receive fasteners for securely coupling the front cover plate 320 to the back cover 340. For example, the slots 324 can be formed at one edge (e.g., the bottom edge) of the front cover plate 320.

The back cover 340 has a substantially open front face 342 and is formed of a top wall 351, a rear wall 360 and a pair of opposing side walls 370. The top wall 351 has a cut-out 352 formed therein to accommodate movement of the gripper unit 400 within the housing 310. The top wall 351 is generally square or rectangular shaped and extends between the side walls 370 and the rear wall 360. The opposing side walls 370 are mirror images of one another and are disposed parallel to and spaced apart from one another. A front edge 372 of each side wall 370 includes a number of fastening tabs 374 that provide mounting surfaces for securely attaching the front cover plate 320 to the back cover 340. Two of the fastening tabs 374 are located at the intersection between the top wall 351 and the side walls 370 and two additional fastening tabs 374 are located below the two tabs 374 at the top wall 351. The illustrated tabs 374 are generally square shaped and are disposed perpendicular to a plane that contains the respective side wall 370. Openings 375 are formed in the fastening tabs 374 for receiving the fasteners and are axially aligned with openings 322 of the front cover plate 320. The side walls 370 also include fastening slots 371 that receive fasteners for securely attaching the side walls 370 to the base plate 350.

The base plate 350 is securely attached to the side walls 370 and the front cover plate 320. The base plate 350 has a shape and is dimensioned in a complementary manner relative to the other parts of the housing 310. The illustrated base plate 350 is generally rectangular shaped and is formed of a body 352 that includes end edges 353 and side edges 354. The end edges 353 have openings 356 formed therein to receive fasteners for coupling the front cover plate 320 to the base plate 350. Similarly, the side edges 354 have openings 357 that receive fasteners for securely coupling the side walls 370 to the base plate 350. The body 352 also includes openings 358 formed therein for securely mounting various components to the base plate 350. For example, the gripper unit 400 is securely attached to the base plate 350 using fasteners that extend through a number of these openings 358.

Any number of different types of materials can be used for the housing 310 and the shape thereof is also likely influenced by design considerations, such as the amount of available space near the dial 130. Thus, the illustrated housing 310 is merely exemplary in nature and not limiting of the present housing 310. For example, the housing 310 can be formed of sheet metal, etc.

The gripper unit 400 is an assembled unit disposed at the third station 150 that is configured to remove the tip cap 40 from the barrel tip 28 of the syringe 10 and place it or park it on the post 161 (FIG. 6). The automated gripper unit 400 is a robotic device or an automated mechanical device and preferably, one exemplary automated gripper unit 400 is a pneumatically operated device; however, the gripper unit 400 can be driven by a motor, etc. The automated gripper unit 400 includes a vertical base 410 which is adjustable in at least several directions. For example, the vertical base 410 has an independent reach (y axis) and vertical axis (x axis) which provides part of the flexibility and motion control that is desirable for the unit 400. The vertical base 410 has an upper end 412 and an opposing lower end 414 which is operatively coupled to other movable components, as will be described hereinafter, to permit the vertical base 410 to move in an up/down direction along the x axis and in lateral directions along the y axis. The upper end 412 is connected to a horizontal support member 420 (e.g., a top bracket) that extends outwardly away from the vertical base 410. In one exemplary embodiment, the lower end 414 is securely attached to a support member 425.

A block member 430 is connected to the horizontal support member 420 and more specifically, the block member 430 is disposed on an underside of the horizontal support member 420 so that it is spaced away from the vertical base 410. The exemplary block member 430 has a block-like shape and is connected to the underside of the horizontal support member 420 by one or more connectors, etc.

The gripper unit 400 has first and second positionable gripper arms 440 which are adjustable in at least one direction and which are coupled to and extend downwardly from the block member 430. For example, each of the gripper arms 440 is movable at least in a direction along the y axis to provide the flexibility and motion control that is desirable in the present system 100. The gripper arms 440 are programmed to work together in tandem so that both arms 440 are driven alike (e.g., either toward each other or away from one another) and at the same time.

The block member 430 can house some of the electronic or pneumatic components and the like that permit the gripper arms 440 to move between the open and closed positions. The coupling between the block member 430 and the gripper arms 440 is such that the gripper arms 440 have the necessary degree of movement to permit the opening and closing thereof.

Each of the gripper arms 440 (FIG. 6) is a generally inverted F-shaped member that is formed of a vertical section 442 and a horizontal gripping section 444 that extends outwardly from one end of the vertical section 442. The gripping section 444 has a cut-out or notch 460 (FIG. 6) formed therein for receiving and gripping a section of the barrel 20 of the syringe 10. Accordingly, the notch 460 has a complementary shape as the shape of the barrel 20. By being movable along at least the y axis, the gripper arms 440 can be positioned between an open position in which the opposing gripping sections of the arms 440 are spaced apart from one another a sufficient distance to permit the tip cap 40 to be received therebetween. In the present invention, the exemplary notch 460 has a "V" shape so that it has sufficient surface area to securely hold the tip cap 40 when the gripping section 444, but not so much that disengaging from tip cap 40 interferes with placement on pin 161 or syringe tip 28. It will be appreciated that the notch 460 can be arcuate in shape as well as being shaped as a serated V, serated semi-circle or a smooth V. Each arm also includes a pair of posts 461 that extend outwardly from the vertical wall 442 toward the open notch 460. The exemplary posts 461 are generally rectangular or square in cross section and they do not extend fully across the width of the gripping section 444. In other words, the post 461 preferably does not extend beyond the leading edge of the gripping section 444. When the tip cap 40 is gripped by the arms 440, the tip cap 40 is disposed between the posts 461 and the gripping sections 444 and more specifically, the tip cap 40 fits between the bottom face of the posts 461 and the upper face of the gripping sections 444. The posts 461 serve to locate the tip cap 40 and make sure that the tip cap 40 remains in the desired gripping position as it is moved from one location to another.

In the closed position, the gripping sections 444 of the arms 440 are brought together so that they either seat against one another or are in very close proximity to one another. When the gripping sections 444 come together in the closed position, the notches 460 define an opening that permits the tip cap 40 to nest within the gripping sections 444.

One knowledgeable in the state of the art will recognize that several motion control devices (i.e., motors, hydraulic drives, pneumatics, etc.) can be used to conduct the linear motion required of the various stations. In the immediate invention, different motion control devices are used for their defined operation. For stations 150 and 180, the motion control devices are powered by pneumatic pressure. Stations 150 and 180 each have three pneumatic motion control devices. For each of these motion control devices, there is a constant pneumatic pressure forcing the certain component to its safe "home" position and a single stage valve that is activated by input from the system controller 470 that over pressurizes the pneumatic cylinder so that the mechanical component can advance to the endstop opposite to its home position.

In the open position of the gripper arms 440, they are spaced sufficiently from one another so as to permit the tip cap 40 to be freely disposed between the gripping sections 444. On an input signal from the control unit 470 (e.g., a programmable actuator, microprocessor, etc.), the gripper arms 440 are driven to the first position. The control unit 470 instructs the gripper unit 400 to perform various operations for removing the tip cap 40 from the barrel tip 28, parking the tip cap 40 on the post 161 and then, using a second controller mechanism, replacing the tip cap 40 on the filled syringe 10. When such an operation is performed, the vertical base 410 is driven in a number of different directions until proper alignment is realized. In other words, the tip cap 40 is disposed between the gripping sections 444 of the opposing arms 440 and more specifically, the gripping sections 444 are disposed adjacent the base section 41 of the tip cap 40 underneath the flange 43 with the notches being aligned with the outer surface of the base section 41. An actuator or the like of the device 400 is then deactivated causing the gripper arms 440 to move inwardly toward one another until the gripping sections 444 seat against the outer surface of the base section 41 of the tip cap 40. In this closed position, the gripper arms 440 apply a force against the base section 41 so that the tip cap 40 is securely held by the gripping sections. When the gripper arms 440 are driven to the closed position, the gripping sections seat against one another and the notches align such that the gripping sections substantially encircle the base section 41.

Since the gripper unit 400 is preferably a pneumatic device, a number of pneumatic controls are disposed near the gripper arms 440. More specifically, the gripper arms 440 are pneumatic devices and therefore, a first pneumatic control 441 is connected to the block member 430. The first pneumatic control 441 is integral to block member 430 and includes first and second flow control valves 443 that are of a point locked type, with the positions set at the time of manufacture. For example, the valves 443 have adjustable knobs that permit a certified field service engineer or technician to adjust the pneumatic pressure that is present at the gripper arms 440 to assist in the opening and closing of the gripper arms 440. As will be appreciated, the unit 400 can be a pneumatically based system since the operation of the vertical base 410 only requires the vertical base 410 to be driven between two fixed positions in one direction of movement.

The gripper unit 400 (FIG. 4) also preferably includes a sensor assembly, generally indicated at 481, for sensing whether a tip cap 40 is present between the gripper arms 440. One exemplary sensor assembly 481 includes a sensor device 483 and a reflector 485 that is spaced therefrom. The sensor device 483 is formed of one or more sensors that are securely attached to a support bracket 489 that is attached to the block member 430. The support bracket 489 has two sections that each has an L-shape and therefore the bracket 489 resembles a series of steps. A bottommost section 491 of the support bracket 489 is the section that holds the one or more sensors 483. The support bracket 489 is disposed so that the gripper arms 440 lie between the support bracket 489 and the vertical base 410.

According to one exemplary embodiment, the sensors 483 are LED type sensors or the like which emit a light beam in a predetermined direction. There are preferably two LED sensors 483 that emit light beams in a direction toward the gripper arms 440 and more specifically, the light beams are targeted between the gripper arms 440 where the tip cap 40 is to be located when the gripper arms 440 properly grip and retain the tip cap 40.

The reflector 485 is securely attached to the vertical base 410 and is axially aligned with the sensors 483 so that when the sensors 483 are actuated, the light beams are emitted from the sensors 483 and, if no obstruction is present, the light beams pass across the space between the support bracket 489 and the inner face of the rear cover 340. If a tip cap 40 is present between the gripper arms 440, then the light beams of the sensors 483 will be impinged or otherwise broken since the tip cap 40 lies within the path of the light beam when it is securely held between the gripper arms 440. When the tip cap 40 is present, the light beams of the sensors 483 do not make contact with the reflector and therefore, the light beams are not reflected back to the sensors 483. Because the sensors 483 are in communication with the control unit 470, a break in the light beam generates a control signal that is delivered to the control unit 470 to indicate that an object, such as the tip cap 40, is present between the gripper arms 440. Conversely, if the gripper arms 440 are instructed to remove the tip cap 40, they are actuated and moved to a position for gripping and retaining the tip cap 40 and if for some reason, the tip cap 40 is not removed properly, then the sensor's light beam is not impinged by the tip cap 40. The light beam of the sensors 483 pass completely to the reflector 485 since there is no tip cap 40 present between the gripper arms 440. The control unit 470 therefore does not receive the control signal indicating the presence of one tip cap 40 between the gripper arms 440. After a predetermined time period, the control unit 470 will reject the syringe 10 if the presence of the tip cap 40 is not detected. Once the syringe 10 is rejected, the dial 130 is advanced and the tip cap process is started over with the next adjacent syringe 10 on the dial 130 being advanced so that it is in position for the gripper unit 400 to act and remove the tip cap 40. If the sensor device 483 detects the presence of a tip cap 40 at a time when the presence is expected, the control signal from the sensor device 483 is received by the control unit 470 and the gripper unit 400 is instructed to continue its process of removing, parking, or replacing the tip cap 40.

The gripper unit 400 includes a number of pneumatic control devices and more specifically, the gripper unit 400 includes a second pneumatic control device 600 and a third pneumatic control device 630. The second pneumatic control device 600 controls movement of the vertical base 410 in towards and out away from the dial 130. In other words, the second pneumatic control device 600 moves the vertical base 410, as well as the gripper arms 440, in a direction toward the dial 130 and in a direction away from the dial 130. The second pneumatic control device 600 is similar to the previously described motion control device 431 with its "home" position being out, away from the dial 130.

In the illustrated embodiment, the second pneumatic control device 600 is disposed at a lower end of the vertical base 410 and preferably is operatively coupled thereto so that actuation of the control device 600 causes the selective, controlled movement of the vertical base 410 in and out from the dial 130. As shown in FIG. 4, both the lower end of the vertical base 410 and the second pneumatic control device 600 are disposed on a support surface 611 of the support member 425. More specifically, the support member 425 has one or more guide tracks 613 formed therein to permit the controlled in and out movement of the vertical base 410. As the vertical base 410 moves in the in and out directions, it moves from one end of the support member 425 to the other end of the support member 425 in a controlled manner so that the gripper arms 440 are moved from an out position, where the gripper arms 440 are disposed away from the dial 130, to an in position, where the gripper arms 440 are disposed above the dial 130 as represented by the syringe 10 in FIG. 6. In this embodiment where pneumatic controls are used, the vertical base 410 travels a fixed distance, namely the distance between the out position and the in position and vice versa.

The second pneumatic control device 600 includes a number of adjustable control features that permit a certified field service engineer or technician to vary the operating parameters of the device 600. For example, the second pneumatic control device 600 can include one or more control valves 602 for controlling and adjusting the pneumatic pressure within the second pneumatic control device 600. In the illustrated embodiment, these control valves 602 are in the form of control knobs that can be easily adjusted by an appropriately certified field service engineer or technician.

The third pneumatic control device 630 controls movement of the vertical base 410 in the up-down directions. In other words, the third pneumatic control device 630 moves the vertical base 410, as well as the gripper arms 440, and the second pneumatic control device 600, in a vertical direction. The third pneumatic control device 630 is similar to the previously described motion control device 431 with its "home" position being up, keeping the gripper mechanism 440 away from the dial 130.

In the illustrated embodiment, the third pneumatic control device 630 is disposed below the support member 625 and therefore is generally below the lower end of the vertical base 410. Preferably, the third pneumatic control device 630 is operatively coupled to the support member 625 so that actuation of the third pneumatic control device 630 causes the selective, controlled movement of the vertical base 410 in up-down directions. As previously specified, one knowledgeable in the state of the art recognizes that controlling the vertical motion of certain components connected to the support member 625 can be accomplished by one of a number of motion controllers (i.e., motors, hydraulic drives, pneumatics, etc.) In the present invention, the up-down movement of the vertical base 410 is caused by a pneumatic cylinder or other moving parts that are pneumatically driven.

As the vertical base 410 moves in the up and down directions, the vertical base 410 is raised and lowered relative to the housing 410 in a controlled manner so that the gripper arms 440 are moved from a raised position, where the gripper arms 440 are disposed a maximum distance away from the upper surface of the dial 130, to a lowered position, where the gripper arms 440 are disposed a minimum distance from the upper surface of the dial 130. This lowered position allows for interaction with the tip cap 40 and either the syringe tip 28 or pin 161. In this embodiment where pneumatic controls are used, the vertical base 410 travels a fixed distance, namely the distance between the raised position and the lowered position and vice versa.

The third pneumatic control device 630 includes a number of adjustable control features that permit a trained and certified field service engineer or technician to vary the operating parameters of the device 630. For example, the third pneumatic control device 630 can include one or more control valves 632 for controlling and adjusting the pneumatic pressure within the third pneumatic control device 630. In the illustrated embodiment, these control valves 632 are in the form of control knobs that can be easily adjusted by the certified field service engineer or technician.

The unit 400 (FIG. 4) also includes a connector module 500 that is disposed within the housing 310 and is securely attached to the base plate 350 using a pair of angled mounting brackets 510. The angled mounting brackets 510 are spaced apart from one another and are mounted to the base plate 350 using fasteners 352 or the like. Each bracket 510 includes a planar surface 512 that has an opening 513 formed therethrough to receive a fastener for mounting a module 520 to the clamps 510. The module 520 is the input/output connector block for the entire station 150. At each end of the module 520, an end stop 524 is provided for limiting the movement of module 520. More specifically, the end stops 524 keep the input/output blocks of the module 520 from sliding off the railed tray to which the module 520 is mounted. The connector module 510 is located adjacent the unit 400 and more specifically, it is located behind the third pneumatic control device 630 (e.g., closer to the rear wall 360). The connector module 510 is thus disposed between the unit 400 and the rear wall 360.

The operation of the gripper unit 400 is now described in detail. To remove a tip cap 40, the third pneumatic control device 630 is deactivated (valves are closed) so that the vertical base 410 and the gripper arms 440 are in the raised position. At the same time, the second pneumatic control device 600 is not actuated (valve closed) and therefore, the vertical base 410 is in the out position. For ease of description, this orientation is referred to as a starting position which permits the dial 130 to be advanced so that one syringe 10 is delivered to a position where the syringe 10 is in axial alignment with the gripper arms 440. The gripper arms 440 are in a closed position in the starting position. In other words, the first pneumatic control 441 is in an deactivated position, thereby causing the two gripper arms 440 to be closed. When the syringe 10 is advanced to a position where the gripper arms 440 are axially aligned with the syringe 10, the syringe 10 likewise is in a start position.

To initiate the tip cap removal cycle, the pneumatic control device 441 is activated so that the gripper arms 440 are opened. The third pneumatic control device 630 is then activated so that the pressure in the valves 632 is released, thereby causing the device 630 to assume the lowered position. In this lowered position, the tip cap 40 of the syringe 10 is disposed between the gripper arms 440 and then the first pneumatic control 441 is deactivated so that the gripper arms 440 are closed and the tip cap 40 is nested within the gripper arms 440. Because of the complementary shape of the gripper arms 440, the tip cap 40 is securely held therebetween and is ready to be removed from the syringe 10.

To remove the tip cap 40 from the syringe 10, the third pneumatic control device 630 is deactivated so that it moves to the raised position. Because the first pneumatic control 441 remains deactivated, the gripper arms 440 remain in engagement with the tip cap 40 as the third pneumatic control device 630 assumes the raised position and this movement in a direction away from the syringe 10 causes the tip cap 40 to be lifted off of the syringe 10 as it is held between the gripper arms 440. It will be appreciated that the sensor device 483 is preferably used to sense whether the tip cap 40 is securely being held by the gripper arms 440. More specifically, the light beam of the sensor 483 is broken when the tip cap 40 comes between the sensor 483 and the reflector 485 and this signals to the controller 470 that an object, e.g., the tip cap 40, is present between the closed gripper arms 440. If the sensor 483 does not detect the presence of a tip cap 40 when the gripper arms 440 are closed in this position, then the controller 470 will cause the vertical base 410 to return to the start position and the removal and parking operations are started again.

Once the third pneumatic control device 630 reaches the raised position, the second pneumatic control 600 is then actuated and this causes the vertical base 410 to go from the out position to the in position. In the in position, the gripper arms 440 holding the tip cap 40 are disposed immediately above the pin (post) 161 for parking of the tip cap thereon. In other words, movement of the vertical base 410 from the out position to the in position causes the gripper arms 440 to move from a position over the syringe 10 to a position over the pin 161. The tip cap 40 is now ready for parking on the pin 161.

To park or place the tip cap 40 on the pin 161, the third pneumatic control device 630 is activated (valve is open) so that the third pneumatic control device 630 moves back to the lowered position. In the lowered position, the gripper arms 440 are immediately above the pin 161. The tip cap 40 is also axially aligned on the pin 161 so that release of the tip cap 40 results in the tip cap 40 being held by the pin 161. To release the tip cap 40, the first pneumatic control 441 is activated (the valve is opened) so that the gripper arms 440 move from the closed position to the open position. As the gripper arms 440 move apart from one another, the tip cap 40 is released from the grip thereof.

Once the tip cap 40 is securely retained on the pin 161, the third pneumatic control device 630 is deactivated so that the vertical base 410 moves from the lowered position to the raised position where the gripper arms 440 are a significant distance from the dial 130. In addition to the actuation of the third pneumatic control device 630, the second pneumatic control device 600 is deactuated resulting in the vertical base 410 moving from the in position to the out position. This movement facilitates the further advancement of the dial 130 and the syringe 10 since the gripper arms 440 are moved away from the dial 130 so as to not obscure access thereto. It will be appreciated that the vertical base 410 has now reassumed the starting position and the process can be repeated by advancing the dial 130 so that another syringe 10 is brought into place and the various components of the gripper unit 400 are then controlled and moved in the manner just previously described for gripping, removing, and parking the tip cap 40 on the pin 161.

As previously mentioned, the sixth station 180 also includes a device 300 for replacing the tip cap 40 on the syringe 10 after the syringe 10 is filled with the medication, etc. at an earlier station, e.g., third station 170. The device 300 that is used at the third station 150 for removing and parking the tip cap 40 from the syringe 10 prior to the syringe being filled is preferably the same type of device as the device 300 that is used at sixth station 180 for retrieving the tip cap 40 from the pin 161 and then replacing it on the syringe 10. The steps of operation are slightly different at the sixth station 180 since the tip cap 40 is initially retained on the pin 161 and not the syringe 10 at this station.

In the starting position at the sixth station 180, the second pneumatic control device 600 is activated, while the first pneumatic control device 441 and the third pneumatic control device 630 are both deactivated (valves are closed) so that the vertical base 410 is in the raised position as well as being in the in position. Thus, the gripper arms 440 are generally above the pin 161 since the vertical base 410 is in the in position. The first pneumatic control 441 is preferably in the closed position so that the gripper arms 440 are closed with respect to one another. The first pneumatic control device 441 is activated and the third pneumatic control device 630 is then activated so that the gripper arms 440 open and the vertical base 410 goes from the raised position to the lowered position. In the lowered position, the gripper arms 440 surround the tip cap 40 that is resting on the pin 161. Next, the first pneumatic control 441 is deactivated resulting in the gripper arms 440 closing and securely capturing and retaining the tip cap 40. In other words, the tip cap 40 nests within the gripper arms 440 and is ready to be removed and lifted from the pin 161. At this point in time, the sensor device 483 is preferably used to determine whether the tip cap 40 is present between the gripper arms 440. If the tip cap 40 is present and is captured between the gripper arms 440, then the light beam of the sensor 483 is broken and a signal is delivered to the controller 470. The controller 470 will then instruct the gripper unit 400 to continue the tip cap replacement operation. If the sensor device 483 does not detect that the tip cap 40 is present between the gripper arms 440, the gripper arms 440 can be instructed to attempt the grasping process again or the controller 470 can be instructed to restart the entire operation by returning the vertical base 410 to the starting position and then the dial 130 is advanced and then process is started over again to attempt to grasp and capture the tip cap 40 from the pin 161 so that it can be replaced onto a filled syringe 10.

To lift the tip cap 40 from the pin 161, the third pneumatic control device 630 is deactivated resulting in the vertical base 410 moving from the lowered position to the raised position. As the vertical base 410 is raised, the tip cap 40 is removed and lifted from the pin 161 since the tip cap 40 is securely held by the gripper arms 440. The vertical base 410 is moved to the raised position and then the second pneumatic control device 600 is activated causing the vertical base 410 to move from the in position to the out position. Thus, the vertical base 410 and the gripper arms 440 thereof are moved away from the dial 130 and the gripper arms 440 are moved from a position where they are disposed over the pin 161 to a position where they are disposed over the uncapped syringe 10. The uncapped syringe 10 has been previously filled with medication and therefore is ready to be capped.

To cap the syringe 10, the third pneumatic control device 630 is activated to cause the vertical base 410 to move from the raised position to the lowered position. When the vertical base 410 moves to the lowered position, the tip cap 40 is press fitted onto the barrel tip 28 of the uncapped syringe 10; however, the tip cap 40 is still securely held between the gripper arms 440. The first pneumatic control 441 is then activated to cause the gripper arms 440 to move from the closed position to the open position. When the gripper arms 440 open, the tip cap 40 is free from the gripper unit 400 and remains fixedly attached to the barrel tip 28 of the syringe 10. The vertical base 410 is then moved to the raised position by deactivating the third pneumatic control device 630 so that the gripper arms 440 are removed from the syringe 10 and are delivered to a position where the gripper arms 440 are disposed above and spaced from the barrel tip 28 of the syringe 10. To start the replacing operation again, the vertical base 410 is returned to the starting position by deactivating the second pneumatic control device 600 to cause the gripper arms 440 to move to the in position so that they are disposed above the dial 130 and more specifically, above the path that the pin 161 follows as the dial 130 advances. The dial 130 is then advanced until a new tip cap 40 is disposed underneath the gripper arms 440 and then the process is started over.

The capped syringe 10 can then be transferred to other stations, such as a station where the syringe in bandolier form is cut into individual syringes 10 that are labeled for particular patients. The syringes 10 can then be unloaded from the dial 130 by a suitable mechanical device. The syringe 10 is then further processed as for example by being delivered to a storage receptacle where it is stored or by being delivered to a transporting device for delivery to the patient.

It will be appreciated by persons skilled in the art that the present invention is not limited to the embodiments described thus far with reference to the accompanying drawings; rather the present invention is limited only by the following claims.

What is claimed is:

1. An automated device for removing a tip cap from an empty syringe, placing the tip cap at a remote location, and replacing the tip cap on a filled syringe, the device comprising:
 a support frame that is movable along at least an x axis and a y axis;
 a gripper mechanism including a pair of gripper arms that are positionable between an open position and a closed position in which the tip cap is securely held therebetween;
 a programmable controller in communication with a plurality of drive actuators that controllably drive the gripper arms and the support frame to desired positions; and
 a sensor for detecting whether the tip cap is disposed between the gripper arms.

2. The automated device according to claim 1, wherein the pair of gripper arms comprise:
 a first automated gripping device for removing a tip cap from a barrel tip of one syringe and placing the removed tip cap at a first location; and
 a second automated gripping device for replacing the removed tip cap on the syringe barrel after medication has been injected therein, wherein each of the first and second automated gripping devices is in communication with the programmable controller and each of the first and second gripping devices moves in at least two directions.

3. The automated device according to claim 1, wherein each of the gripping arms has a platform with a shaped cut out formed at one edge thereof and the two shaped cut outs are aligned with one another so that when the gripper arms are in the closed position, the shaped cut outs define an opening that is sized to receive and hold the tip cap.

4. The automated device according to claim 1, wherein each of the first and second automated gripper arms is movable along an x axis and a y axis.

5. The automated device according to claim 1, wherein the plurality of drive actuators has a first control mechanism for controlling opening and closing of gripper arms that grasp and retain the tip cap; a second control mechanism for controlling up and down movement of the gripper arm and a third control mechanism for controlling inward and outward movement of the gripper arm.

6. The automated device according to claim 5, wherein each of the first, second and third control mechanisms is a pneumatic device that upon actuation causes movement of the device in at least one direction.

7. The automated device according to claim 5, wherein each of the first and second automated gripper arms includes a vertical base with the gripper arms being disposed closer to an upper end of the vertical base, the second control mechanism operatively connected to the vertical base to cause controlled up and down movements thereof; the third control mechanism operatively connected to the vertical base to cause controlled inward and outward movements thereof.

8. The automated device according to claim 7, wherein second and third control mechanisms are one of pneumatic devices and mechanical motorized devices that each moves the vertical base between two positions.

9. The automated device according to claim 5, wherein the gripper arm is positionable between a starting position, a second position where the tip cap is grasped by the gripper arms for removal from the syringe and a third position where the tip cap is disposed over a feature for retainingly parking the tip cap.

10. The automated device according to claim 9, wherein the feature comprises a post that is formed as part of the support for receiving and holding the removed tip cap.

11. The automated device according to claim 1, further including an automated rotary device that is indexed to advance the syringe from one station to another station, the rotary device having a feature for holding the removed tip cap as the syringe is advanced from one station to the next.

12. The automated device according to claim 1, wherein the support frame comprises a vertical base that is operatively connected to a first control unit that moves the vertical base in a track along the y axis between inward and outward positions and a second control unit that moves the vertical base along the x axis between raised and lowered positions.

13. The automated device according to claim 1, wherein the gripper mechanism is operatively connected to a control unit that positions the gripper arms between the open and closed positions.

14. The automated device according to claim 1, wherein the sensor comprises a reflecting light emitting diode (LED).

15. The automated device according to claim 1, wherein the sensor is of a type that emits a light beam and a reflector is provided across from the sensor for reflecting the light beam, the sensor device being mounted relative to gripper arms that grasp and retain the tip cap so that the light beam passes through a space between the gripper arms where the tip cap is received, the sensor device in communication with the programmable controller so that a control signal is delivered to the programmable controller when the tip cap is disposed within the space, thereby impinging the light beam.

16. The automated device according to claim 1, wherein the plurality of drive actuators comprises a first pneumatic control device for controllably moving the support frame along the y axis and a second pneumatic control device for controllably moving the support frame along the x axis.

17. The automated device according to claim 1, wherein the plurality of drive actuators comprises a first motorized mechanical device mechanism for controllably moving the support frame along the y axis and a second motorized mechanical device mechanism for controllably moving the support frame along the x axis.

18. The automated device according to claim 1, wherein the support frame comprises a vertical base.

19. The automated device according to claim 1, wherein the controller and sensor are configured such that if the sensor detects that the tip cap is not securely attached to a barrel of the syringe, then the syringe is rejected and is not filled at the filling station; and if the sensor device detects the presence of a tip cap, then the syringe is subjected to at least one device for automatically removing, parking the tip cap, filling the syringe and replacing the tip cap.

20. An automated device for removing a tip cap from a barrel of an empty syringe, placing the tip cap at a remote location, and replacing the tip cap on a filled syringe, the device comprising:

a support frame that is movable along at least an x axis and a y axis;

a gripper mechanism including a pair of gripper arms that are positionable between an open position and a closed position in which the tip cap is securely held therebetween;

a programmable controller in communication with a plurality of drive actuators that controllably drive the gripper arms and the support frame to desired positions; and a sensor for detecting whether the tip cap is securely attached to the syringe barrel and if the sensor detects that the tip cap is not securely attached to the syringe barrel, then the programmer rejects the syringe and prevents the syringe barrel from being filled; and if the sensor device detects the presence of a tip cap, then the syringe is subjected to at least one device for automatically removing, parking the tip cap, filling the syringe and replacing the tip cap.

* * * * *

(12) INTER PARTES REEXAMINATION CERTIFICATE (0139th)
United States Patent
Osborne et al.

(10) Number: US 7,017,622 C1
(45) Certificate Issued: Jan. 19, 2010

(54) AUTOMATED MEANS FOR REMOVING, PARKING AND REPLACING A SYRINGE TIP CAP FROM A SYRINGE

(75) Inventors: Joel A. Osborne, Oklahoma City, OK (US); William C. Aven, Edmond, OK (US); Dennis Tribble, Oklahoma City, OK (US)

(73) Assignee: ForHealth Technologies, Inc., Daytona Beach, FL (US)

Reexamination Request:
No. 95/000,345, Feb. 11, 2008

Reexamination Certificate for:
Patent No.: 7,017,622
Issued: Mar. 28, 2006
Appl. No.: 10/426,910
Filed: Apr. 30, 2003

Related U.S. Application Data
(60) Provisional application No. 60/430,481, filed on Dec. 3, 2002.

(51) Int. Cl.
B65B 1/04 (2006.01)
B65B 3/12 (2006.01)

(52) U.S. Cl. .................... 141/27; 141/94; 604/407; 604/416

(58) Field of Classification Search .................... None
See application file for complete search history.

(56) References Cited

U.S. PATENT DOCUMENTS

| | | |
|---|---|---|
| 2,988,984 A | 2/1961 | Eckert et al. |
| 3,002,387 A | 10/1961 | Micheletti |
| 3,556,342 A | 1/1971 | Guarr |
| 3,965,945 A | 6/1976 | Ross |
| 4,058,121 A | 11/1977 | Choksi et al. |
| 4,372,464 A | 2/1983 | Otten |
| 4,669,599 A | 6/1987 | Dijkmeijer et al. |
| 4,699,186 A | 10/1987 | Palin et al. |
| 4,706,207 A | 11/1987 | Hennessy et al. |
| 4,835,707 A | 5/1989 | Amano et al. |
| 4,847,764 A | 7/1989 | Halvorson |
| 4,878,705 A | 11/1989 | Arnquist |
| 5,004,962 A | 4/1991 | Fonss et al. |
| 5,229,074 A | 7/1993 | Heath et al. |
| 5,288,285 A | 2/1994 | Carter |
| 5,324,519 A | 6/1994 | Dunn et al. |
| 5,341,854 A | 8/1994 | Zezulka et al. |
| 5,363,885 A | 11/1994 | McConnell et al. |
| 5,366,896 A | 11/1994 | Margrey et al. |
| 5,411,489 A | 5/1995 | Pagay et al. |
| 5,431,201 A | 7/1995 | Torchia et al. |
| 5,451,528 A | 9/1995 | Raymoure et al. |
| 5,479,969 A | 1/1996 | Hardie et al. |
| 5,522,512 A | 6/1996 | Archer et al. |
| 5,522,804 A | 6/1996 | Lynn |
| 5,769,086 A | 6/1998 | Ritchart et al. |
| 5,797,515 A | 8/1998 | Liff et al. |
| 5,884,457 A | 3/1999 | Ortiz et al. |
| 5,895,019 A * | 4/1999 | Ibarra .................... 248/288.11 |
| 5,911,252 A | 6/1999 | Cassel |
| 5,948,360 A | 9/1999 | Rao et al. |
| 6,082,987 A * | 7/2000 | Su et al. .................... 425/150 |
| 6,200,289 B1 | 3/2001 | Hochman et al. |
| 6,249,717 B1 | 6/2001 | Nicholson |
| 6,343,690 B1 | 2/2002 | Britton et al. |
| 2001/0018937 A1 | 9/2001 | Nemoto |
| 2002/0020459 A1 | 2/2002 | Baldwin et al. |
| 2002/0035412 A1 | 3/2002 | Kircher et al. |

FOREIGN PATENT DOCUMENTS

WO    WO 90/09776    9/1990

* cited by examiner

*Primary Examiner*—Glenn K. Dawson

(57) ABSTRACT

In one exemplary embodiment, an automated syringe preparation mechanism for an automated medication preparation system is provided and the mechanism includes (1) a first automated gripping mechanism having a pair of adjustable gripper arms for removing a tip cap from a barrel of one syringe and placing the removed tip cap at a first location and (2) a second automated gripping mechanism having a pair of adjustable gripper arms for replacing the removed tip cap on the syringe barrel after the medication is injected therein.

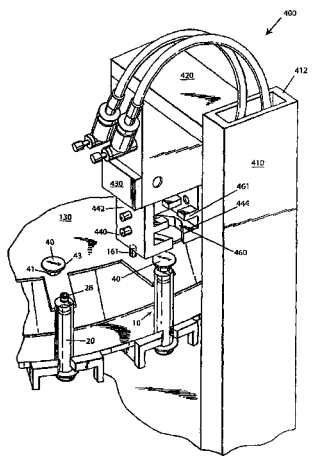

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1–20 are cancelled.

* * * * *